United States Patent [19]
Townsend

[11] Patent Number: 5,549,574
[45] Date of Patent: Aug. 27, 1996

[54] CARTRIDGE ASSEMBLY FOR USE IN A PEN-TYPE MEDICAMENT INJECTOR

[75] Inventor: Michael W. Townsend, Amesbury, Mass.

[73] Assignee: Eli Lilly and Company, Indianapolis, Ind.

[21] Appl. No.: 298,117

[22] Filed: Aug. 30, 1994

[51] Int. Cl.[6] .................................................. A61M 5/00
[52] U.S. Cl. ........................ 604/232; 604/416; 604/903; 366/129; 366/317; 366/332; 215/DIG. 8; 215/DIG. 3; 206/219; 206/221
[58] Field of Search ............................ 604/232, 218, 604/82, 89, 90, 234, 228, 220–222, 91, 225, 244, 256, 199–202, 80–91, 416, 903, 205, 206, 219–222; 366/129, 256, 289, 317, 332; 215/DIG. 3, DIG. 8

[56] References Cited

U.S. PATENT DOCUMENTS

| | | | |
|---|---|---|---|
| 679,198 | 7/1901 | Witkowski | 604/232 |
| 1,279,223 | 9/1918 | Barry . | |
| 1,660,974 | 2/1928 | Porro . | |
| 1,668,088 | 5/1928 | Russell . | |
| 2,816,743 | 12/1957 | Kirkland . | |
| 3,122,357 | 2/1964 | Roch . | |
| 3,331,538 | 7/1967 | Higgins | 604/222 |
| 3,578,291 | 5/1971 | Oberli . | |
| 4,148,619 | 4/1979 | Deutsch . | |
| 4,150,089 | 4/1979 | Linet . | |
| 4,382,685 | 5/1983 | Pearson . | |
| 4,494,878 | 1/1985 | Rainey, Jr. . | |
| 4,715,854 | 12/1987 | Vaillancourt | 604/89 |
| 4,850,966 | 7/1989 | Grau et al. | 604/82 |
| 4,916,672 | 4/1990 | McCrory . | |
| 5,007,903 | 4/1991 | Ellard | 604/220 |
| 5,017,190 | 5/1991 | Simon et al. | 604/207 |
| 5,041,088 | 8/1991 | Ritson et al. | 604/82 |
| 5,104,380 | 4/1992 | Holman et al. | 604/117 |
| 5,240,322 | 8/1993 | Haber et al. | 604/416 |
| 5,314,416 | 5/1994 | Lewis et al. | 604/219 |
| 5,360,410 | 11/1994 | Wacks | 604/232 |
| 5,376,072 | 12/1994 | Klearman et al. | 604/218 |
| 5,411,488 | 5/1995 | Pagay et al. | 604/232 |

Primary Examiner—John D. Yasko
Assistant Examiner—Ronald K. Stright, Jr.
Attorney, Agent, or Firm—Woodard, Emhardt, Naughton Moriarty & McNett

[57] ABSTRACT

A cartridge assembly for use in a pen-type medicament injector includes a cartridge for holding a medicament suspension with an open end and an opposite capped end configured to receive a needle therethrough to permit the exit of the medicament suspension, and includes a plunger sized to be received and to seal the open end and to be telescopically movable therein, and the plunger defining a top surface and including at least one monolithic mixing vane formed therefrom and extending from the top surface and inwardly of the cartridge when the plunger is sealingly engaged with the open end.

20 Claims, 2 Drawing Sheets

U.S. Patent    Aug. 27, 1996    Sheet 1 of 2    5,549,574
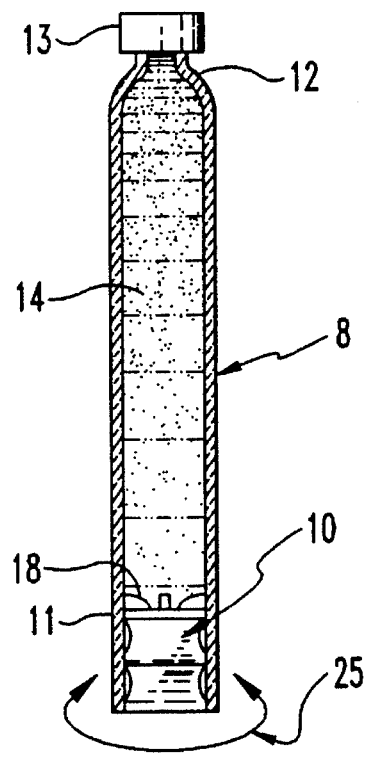
Fig. 1
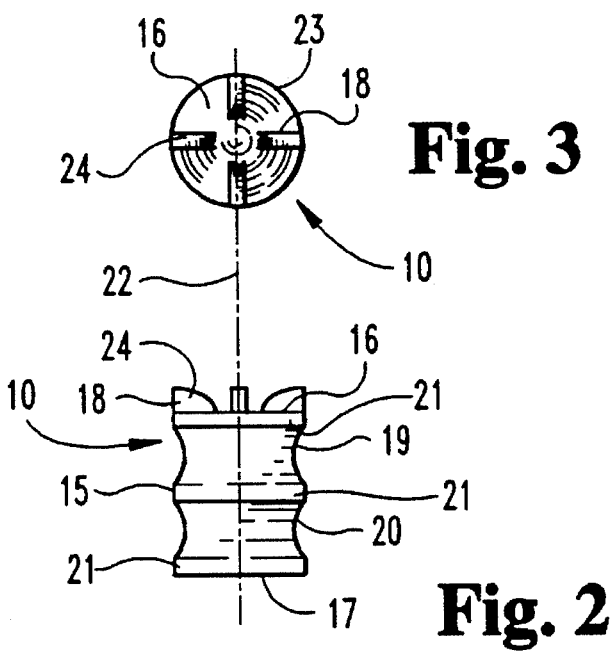
Fig. 3
Fig. 2

CARTRIDGE ASSEMBLY FOR USE IN A PEN-TYPE MEDICAMENT INJECTOR

FIELD OF THE INVENTION

The present invention refers to devices for administering medicaments, and more particularly to a cartridge assembly for use in a pen-type medicament injector, the cartridge assembly including a plunger with integral mixing vanes.

BACKGROUND OF THE INVENTION

According to the American Diabetes Association, there are roughly 14 million diabetics in the United States, with about 7 million having been diagnosed. Of the seven million diagnosed patients, about 105 thousand are treated with injectable insulin, and the rest with weight loss, diet and oral antidiabetic drugs.

Some of the injectable insulin dosage forms are a crystalline suspension, an amorphous, non-crystalline suspension and a combination suspension containing both crystalline and amorphous forms. These are provided in a generally bell-shaped vial. Prior to each injection, the vial is shaken to agitate the liquid suspension, thereby putting any crystals or amorphous particles which may have settled, back into suspension. Because of the vial's shape and because there is gas inside the vial along with the liquid suspension, little agitation of the vial is required to insure sufficient re-suspension of the suspension particles.

With the introduction of pen-like syringes, insulin injection became less complicated and less of a spectacle for the user. Unfortunately, mixing of the insulin to re-suspend the suspension particles became more difficult. The pen-like syringes currently available include a generally cylindrical ampule or cartridge containing the insulin in an essentially bubble-free crystalline suspension. The cartridge has a needle-pierceable cap at one end and a piston or plunger sealing the opposite, open end. The pen-like syringe holds the cartridge, and has a mechanism for advancing a piston rod a pre-determined distance against the bottom side of the cartridge plunger. This forces a corresponding pre-determined dosage of the suspension through the needle. Absent a gas bubble (which is either absent initially or has been ejected from the cartridge prior to the first use), the pen-like syringe and its medicament filled cartridge can be used multiple times to deliver precise, pre-determined dosages. Devices of this type are described in U.S. Pat. Nos. 5,017,190 and 5,104,380.

Because of the shape of the cartridge and the absence of a gas bubble within the cartridge, the ability to quickly agitate the suspension in the cartridge is significantly reduced as compared to the conventional, bell-shaped vial. The contents of the cartridge all have substantially the same density, and shaking, rocking or twisting the cartridge does not impart changes in momentum to the different elements therein sufficient to produce the necessary mixing. One device which has addressed this problem is discussed in U.S. Pat. No. 4,850,966, wherein at least one inert mixing element such as a glass bead is provided inside the cartridge along with the suspension. Because the glass bead has a different density than the suspension, shaking the cartridge causes the glass bead to move within the cartridge and thereby effectively agitate the contents. Unfortunately, the bead takes up space otherwise available for the medicament; the bead reduces the distance that the plunger may be advanced toward the needle end of the cartridge; and the bead represents another element to be manufactured and manipulated in the assembly of the cartridge.

What is needed is an alternative device for insuring proper mixing of the suspension within the cartridge of a pen-type syringe.

DESCRIPTION OF THE DRAWINGS

FIG. 1 is a side cross-sectional view of a cartridge 8 for delivering a liquid from a pen-type syringe in accordance with the preferred embodiment of the present invention.

FIG. 2 is an elevational view of plunger 10 of the cartridge 8 shown in FIG. 1.

FIG. 3 is a plan view of the plunger 10 of FIG. 2.

SUMMARY OF THE INVENTION

Figure 4:
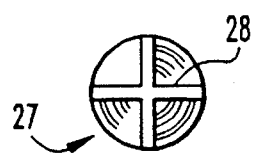
FIGS. 4 and 5 are plan and elevational views, respectively, of an alternative embodiment plunger 27 for use with the cartridge 8 shown in FIG. 1.

Generally speaking, there is provided a cartridge assembly for use in a pen-type medicament suspension injector. The cartridge assembly includes a cylindrical cartridge having an open end and an opposite capped end configured to receive a needle therethrough. The cartridge assembly further includes a plunger sized to be received within and to tightly seal the open end and to be telescopically movable therein. The plunger defines a top surface and includes one or more upstanding monolithic mixing vanes formed therefrom and extending from the top surface and into the liquid medicament. When the cartridge is twisted back and forth about its axis, the vanes help create small currents and eddies within the cartridge contents to facilitate insuring that the contents are properly mixed.

It is an object of the present invention to provide an improved apparatus for holding and delivering liquid medicaments in a pen-type syringe.

It is another object of the present invention to provide a device for facilitating the agitation of the liquid contents in a cylindrical cartridge usable with a pen-type syringe.

Other objects and advantages of the present invention will become apparent from the following description of the preferred embodiment.

DESCRIPTION OF THE PREFERRED EMBODIMENT

For the purposes of promoting an understanding of the principles of the invention, reference will now be made to the embodiments illustrated in the drawings and specific language will be used to describe the same. It will nevertheless be understood that no limitation of the scope of the invention is thereby intended, and that further applications of the principles of the invention as illustrated therein being contemplated as would normally occur to one skilled in the art to which the invention relates.

Referring to FIG. 1 there is shown a cartridge 8 for use in a conventional pen-type syringe (not shown) in accordance with the preferred embodiment of the present invention. Cartridge 8 is substantially cylindrical with one open end 11 adapted to telescopically receive a piston 10, and with an opposite restricted diameter end 12 which is tightly sealed by an outlet cap 13. Cap 13 is of the type commonly used with medicament containers, and has a rubber or other suitable core through which a double pointed needle may be extended to access the medicament 14.

Referring to FIGS. 2 and 3, plunger 10 has a main body 15, an upper end 16, a lower end 17 and a number of mixing vanes 18. Body 15 is generally cylindrical and defines a pair of annular recesses 19 and 20, each of which has a generally arcuate cross-section. Above and below annular recesses 19 and 20, body 15 defines three annular tube-engaging sealing rings 21 which are sized and shaped to engage and seal with the interior surface of cartridge 8. If desired, the body 15 of plunger 10 may be configured to have a fewer or greater number of sealing rings 21, and the recesses 19 and 20 between each pair of sealing rings 21 may be shaped other than as shown in FIG. 2. The primary goal is that sealing rings 21 properly seal against the inside of cartridge 8, yet not offer excessive resistance against the movement of plunger 10 through cartridge 8 and toward cap 13 during operation of the conventional pen-type syringe (not shown).

Extending upwardly from the top of plunger 10 are four identical vanes 18, spaced 90° apart about the axis 22 of plunger 10. Each vane 18 is shaped generally as a quarter section of an ellipse, that is, as a bulging triangle with the hypotenuse portion 24 thereof sloping downwardly and radially inwardly toward axis 22. The vanes 18 collectively do not extend all the way to the center of top 16, but rather extend from points radially away from axis 22, and radially therefrom to the outer periphery 23 of top 16.

In use, cartridge 8 contains the desired medicament 14, such as recombinant human insulin, with plunger 10 firmly lodged in the open end 11 of cartridge 8. Preferably, there is no gas inside cartridge 8 along with the medicament 14. When it is desired to mix the contents 14, cartridge 8 is placed between the palms of one's hands with plunger 10 pointing down, vanes 18 thereby extending upwardly. Cartridge 8 is then rolled back and forth between the palms, with cartridge 8 and plunger 10 thereby being rotated back and forth about their common axis 22 as shown at 25 (FIG. 1). In the case of a conventional plunger, without mixing vanes 18, the fluid contents within the cartridge would tend not to rotate along with the surrounding cartridge and plunger due to inertial effects. In contrast, when cartridge 8 and its plunger 10 with vanes 18, in accordance with the present invention, is rotated as described, the vanes 18 interact with the contents 14 to create little currents and eddies to help agitate the contents 14.

Figure 5:
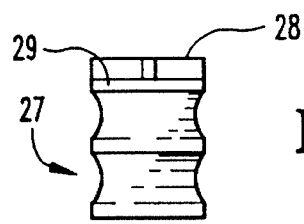
Figure 6:
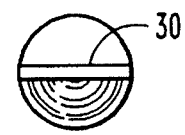
FIGS. 6 and 7 are plan and elevational views, respectively, of an alternative embodiment plunger 32 for use with the cartridge 8 shown in FIG. 1.
Figure 7:
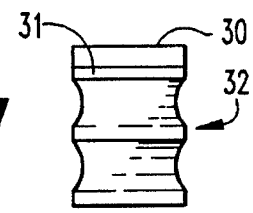
Figure 8:
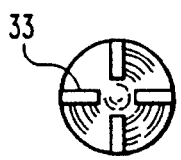
FIGS. 8 and 9 are plan and elevational views, respectively, of an alternative embodiment plunger 36 for use with the cartridge 8 shown in FIG. 1.
Figure 9:
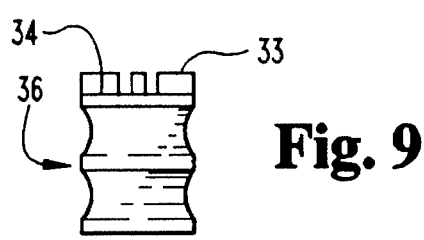
Figure 10:
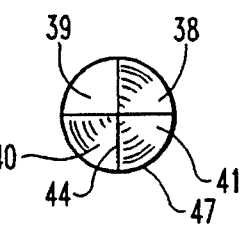
FIGS. 10 and 11 are plan and elevational views, respectively, of an alternative embodiment plunger 37 for use with the cartridge 8 shown in FIG. 1.
Figure 11:
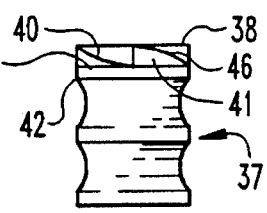
Figure 12:
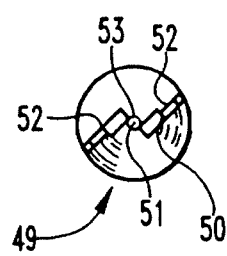
FIG. 12 is a plan view of an alternative embodiment plunger 49 for use with the cartridge 8 shown in FIG. 1.

Alternative embodiments are shown in FIGS. 4-12. In FIGS. 4 and 5, the plunger 27 includes a single vane 28 which extends upwardly from the top surface 29 in the shape of a cross. In FIGS. 6 and 7, a single vane 30 extends upwardly from the top surface 31 of a plunger 32, the vane having a generally rectangular shape, extending diametrically across the top surface 31. In FIGS. 8 and 9, four separate, generally rectangular shaped vanes 33 extend upwardly from the top surface 34 of a plunger 36. The vanes 33 extend radially outwardly, but do not connect at the central axis. The plunger 37 shown in FIGS. 10 and 11 has four vanes 38, 39, 40 and 41 which extend upwardly from the top end 42 of plunger 37. Each of the vanes 38 through 41 is ramped. That is, for example, vane 41 has a triangular polyhedron shape with the outer corner rounded off by the circular periphery 47. A ramped face 46 extends down from the top of wall 44 in a direction perpendicular to the wall 44 of the next adjacent vane (38) until terminated by the circular, circumferential periphery 47. In FIG. 12, plunger 49 is identical to the plunger 36 shown in FIGS. 8 and 9, except with each of the four vanes 33 rotated about axes 50 which pass through the center of each vane and which are parallel to the central axis 51 of plunger 49. The resulting vanes 52 extend outwardly, not radially, but tangentially from an imaginary circle 53 centered therebetween and coaxial to axis 51. Circle 53 may have a radius between zero and the outer diameter of the top surface of plunger 49. It is believed that optimum results are achieved in this design when circle 53 has a diameter between one tenth and one fifth of the diameter of the top surface.

Other embodiments of plungers are contemplated by the present invention whereby the vanes have various configurations, all of which include the vanes extending upwardly from the top surface (16 of FIG. 3, 29 of FIG. 5, 45 of FIG. 11, etc.). While the heights of the vanes described herein may vary as desired, it is believed that they must extend upwardly at least 0.4 mm from the top surface to create a significant agitating effect. In one embodiment, the vanes of a cartridge plunger with a diameter of 6.5 mm extend at least 1 mm upwardly from their top surface. For cartridges of varying diameters, the vanes should have a vertical height equal to or greater than 1/16th the diameter of the plunger. It is believed that optimum results are achieved when each vane extends upwardly a distance equal to approximately one sixth the diameter of the plunger. It is also preferred that each mixing vane have its greatest height at the outer periphery.

While the present invention has been described to be used with liquid suspension medicaments in a cylindrical cartridge, the plunger with upstanding mixing vanes may be adapted for use with other medicament containers to enhance the ability to quickly and efficiently mix the container contents. Also, while each of the embodiments described and shown herein provides that the mixing vanes extend substantially perpendicularly upward from the top surface of the plunger, embodiments are contemplated wherein the mixing vanes form an angle with the top surface of the plunger other than 90°.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected.

What is claimed is:

1. A cartridge assembly for use in a pen-type medicament injector, comprising:

a cartridge for holding liquid medicament and having an open end and having an opposite capped end, the opposite capped end comprising a pierceable material operable to seal shut the capped end and to receive a needle therethrough to permit the exit of the liquid medicament; and a plunger sized to be received and to seal the open end and to be telescopically movable within the cartridge, said plunger defining a top surface and including at least one monolithic mixing vane formed therefrom and extending from said surface and inwardly of said cartridge when said plunger is sealingly engaged within the open end.

2. The cartridge assembly of claim 1 wherein the top surface defines a circumferential periphery and said plunger has a central axis and said at least one mixing vane has a height which is greater nearer to the circumferential periphery than to the central axis.

3. The cartridge assembly of claim 2 wherein said at least one mixing vane has the shape of a one-quarter section of an ellipse.

4. The cartridge assembly of claim 3 wherein there are four of said at least one mixing vanes.

5. The cartridge assembly of claim 1 wherein the top surface has a diameter and said at least one mixing vane has a height equal to or greater than one sixteenth of the diameter of the top surface.

6. The cartridge assembly of claim 5 wherein the height of said at least one mixing vane is equal to or greater than one sixth the diameter of the top surface.

7. The cartridge assembly of claim 1 wherein said plunger has a central axis and there are four of said at least one mixing vanes, the four mixing vanes extending radially and being circumferentially spaced about the axis.

8. The cartridge assembly of claim 7 wherein said top surface is substantially flat and perpendicular to the central axis.

9. The cartridge assembly of claim 1 wherein the top surface defines a circumferential periphery and a diameter, and wherein said plunger has a central axis and wherein said at least one mixing vane includes two generally rectangular mixing vanes, and wherein each mixing vane extends tangentially toward the outer periphery from a circle coaxial with the central axis and having a diameter greater than zero and less than the diameter of the top surface.

10. The cartridge assembly of claim 9 wherein the circle has a diameter between one tenth and one fifth of the diameter of the top surface.

11. The cartridge assembly of claim 9 wherein each mixing vane has a height which is greater at points farther from the central axis than nearer to the central axis.

12. The cartridge assembly of claim 1 wherein the top surface defines a circumferential periphery and said at least one mixing vane extends radially outwardly to the periphery.

13. The cartridge assembly of claim 1 wherein said at least one mixing vane is a single, rectangular shaped vane extending diametrically across the top surface of said plunger.

14. The cartridge assembly of claim 1 wherein the top surface defines a circumferential periphery and wherein said at least one mixing vane is a single vane in the shape of a cross extending radially outwardly to the circumferential periphery.

15. The cartridge assembly of claim 1 wherein the top surface defines a circumferential periphery and said at least one mixing vane includes four ramped mixing vanes each having the shape of a triangular polyhedron with the outer corner rounded off by the circumferential periphery.

16. The cartridge assembly of claim 1 wherein said cartridge contains a medicament suspension and is essentially bubble-free.

17. A cartridge assembly for use in a pen-type medicament injector, comprising:

a cylindrical cartridge for holding liquid medicament and having a first sealed end and an opposing open end, the first sealed end comprising a pierceable material operable to seal shut the first end, but to permit a needle to pierce and extend through the material and into the cartridge to access the medicament; and a plunger sized to be received and seal the open end and to be telescopically movable within said cartridge, said plunger defining a top surface and having at least one monolithic mixing vane formed therefrom and extending upwardly from said top surface to a height of at least 0.4 mm.

18. The cartridge assembly of claim 17 wherein there are four mixing vanes extending radially from the central axis.

19. A cartridge assembly for use in a pen-type medicament injector, comprising:

a cylindrical cartridge for holding liquid medicament and having a first sealed end and an opposing open end, the first sealed end comprising a pierceable material operable to seal shut the first end, but to permit a needle to pierce and extend through the material and into the cartridge to access the medicament; and a plunger sized to be received and seal the open end and to be telescopically movable within said cartridge, said plunger defining a top surface and having at least one mixing vane extending upwardly from the top surface to form an angle with the top surface which is less then 90°.

20. A cartridge assembly of claim 19 wherein there are four mixing vanes extending upwardly from the top surface and forming angles with the top surface which are less than 90°.

* * * * *